(12) United States Patent
Löfvendahl (10) Patent No.: US 11,167,233 B2
(45) Date of Patent: Nov. 9, 2021

(54) CABIN FILTER CLEANING SYSTEMS AND METHODS FOR A VEHICLE

(71) Applicant: Volvo Car Corporation, Gothenburg (SE)

(72) Inventor: Anders Löfvendahl, Gothenburg (SE)

(73) Assignee: Volvo Car Corporation, Gothenburg (SE)

( * ) Notice: Subject to any disclaimer, the term of this patent is extended or adjusted under 35 U.S.C. 154(b) by 222 days.

(21) Appl. No.: 16/542,414

(22) Filed: Aug. 16, 2019

(65) Prior Publication Data

US 2021/0046411 A1    Feb. 18, 2021

(51) Int. Cl.
*B01D 46/00* (2006.01)
*A61L 9/20* (2006.01)
(Continued)

(52) U.S. Cl.
CPC .......... *B01D 46/0061* (2013.01); *A61L 9/205* (2013.01); *B01D 46/0028* (2013.01); *B01D 46/0036* (2013.01); *B01D 46/0038* (2013.01); *B01D 53/007* (2013.01); *B01D 53/04* (2013.01); *B01D 53/885* (2013.01); *B01J 21/063* (2013.01); *B01J 35/004* (2013.01); *B60H 3/0633* (2013.01); *A61L 2209/12* (2013.01); *A61L 2209/14* (2013.01); *B01D 2253/102* (2013.01); *B01D 2255/802* (2013.01); *B01D 2257/90* (2013.01); *B01D 2259/4566* (2013.01); *B01D 2259/804* (2013.01); *B01D 2279/50* (2013.01); *B60H 2003/0675* (2013.01); *B60H 2003/0691* (2013.01)

(58) Field of Classification Search
CPC .. B01D 46/0061; B01D 46/0028; A61L 9/205
See application file for complete search history.

(56) References Cited

U.S. PATENT DOCUMENTS

2019/0063763 A1\* 2/2019 Kleinberger ............ F24F 8/192
2019/0240371 A1\* 8/2019 Benedek ............ B01D 46/0028
2020/0061231 A1\* 2/2020 Jeong ................. B01D 46/0004

FOREIGN PATENT DOCUMENTS

CN           2918131 Y      7/2007
KR        200432637 Y1    12/2006
(Continued)

*Primary Examiner* — Kevin Joyner
(74) *Attorney, Agent, or Firm* — Clements Bernard Walker; Christopher L. Bernard (57) ABSTRACT

Systems and methods that utilize both UVA and UVC lamps to clean and disinfect a cabin filter of a vehicle, thereby preventing the cabin filter from becoming fouled for an extended period of time. By performing both gas filtration and cabin filter disinfection functions, these systems and methods mitigate: (1) the pressure drop (or flow reduction) experienced; (2) the smell breakthrough when the gas adsorbent becomes saturated; and (3) the presence of microbial growth. This is accomplished by the sequential application of UVC and UVA radiation to the cabin filter, with the UVC radiation being applied for a period of time upon vehicle startup to neutralize bacteria and fungus present in the cabin filter and the UVA radiation subsequently being applied continuously to filter the gas flowing through the cabin filter. A photocatalyst may be added to the cabin filter itself to enhance disinfection and gas filtration.

20 Claims, 4 Drawing Sheets

(51) Int. Cl.
    *B01D 53/04*     (2006.01)
    *B01D 53/00*     (2006.01)
    *B01D 53/88*     (2006.01)
    *B60H 3/06*     (2006.01)
    *B01J 21/06*     (2006.01)
    *B01J 35/00*     (2006.01)

(56) References Cited

FOREIGN PATENT DOCUMENTS

| KR | 20180036517 A | 4/2018 |
|----|---------------|--------|
| WO | 20030086792 A1 | 10/2003 |
| WO | 201800234633 A1 | 12/2018 |

* cited by examiner

CABIN FILTER CLEANING SYSTEMS AND METHODS FOR A VEHICLE

TECHNICAL FIELD

The present disclosure relates generally to the automotive and environmental control fields. More particularly, the present disclosure relates to cabin filter cleaning systems and methods for a vehicle.

BACKGROUND

In a vehicle, a cabin filter must be replaced periodically. This cabin filter is responsible for cleaning the air breathed by the driver and passengers in the passenger compartment and it is undesirable for such cabin filter to become fouled. The lifespan of the cabin filter is generally dependent upon three factors: (1) the pressure drop (or flow reduction) experienced; (2) the smell breakthrough when the gas adsorbent becomes saturated; and (3) the presence of microbial growth. In some markets, with relatively clean air, the pressure drop (or flow reduction) is less of a factor, while the smell breakthrough and the presence of microbial growth remain significant factors. The need for frequent replacement of the cabin filter (every 20,000 miles or once a year) can become a hassle, especially in fleet vehicles, for example, resulting in significant service time and expense. Thus, systems and methods for cleaning a cabin filter are desirable.

Ultraviolet (UV) lamps have been used in various contexts to clean/disinfect both liquids and solids. Such cleaning/disinfection is typically carried out using ultraviolet-A (UVA) lamps in the 315-400 nm range, as such UVA lamps are available as compact and inexpensive light-emitting diodes (LEDS). As described in greater detail herein below, these UVA lamps may be used generally in gas filtration applications. Ultraviolet-C (UVC) lamps in the 100-280 nm range, previously only available as bulky and expensive mercury (Hg) lamps, are now also available as compact and inexpensive LEDs. As also described in greater detail herein below, these UVC lamps may be used generally in antibacterial and antifungal applications.

Thus, what are needed in the art are systems and methods that utilize both UVA and UVC lamps to clean and disinfect a cabin filter of a vehicle, thereby preventing the cabin filter from becoming fouled for an extended period of time.

SUMMARY

In various exemplary embodiments, the present disclosure provides systems and methods that utilize both UVA and UVC lamps to clean and disinfect a cabin filter of a vehicle, thereby preventing the cabin filter from becoming fouled for an extended period of time. By performing both gas filtration and cabin filter disinfection functions, these systems and methods mitigate: (1) the pressure drop (or flow reduction) experienced; (2) the smell breakthrough when the gas adsorbent becomes saturated; and (3) the presence of microbial growth. This is accomplished by the sequential application of UVC and UVA radiation to the cabin filter, with the UVC radiation being applied for a period of time upon vehicle startup to neutralize bacteria and fungus present in the cabin filter and the UVA radiation subsequently being applied continuously to filter the gas flowing through the cabin filter. Limiting the application of the UVC radiation in this manner prevents damage to the cabin filter that might otherwise occur, as the polymer of the cabin filter can be readily stabilized with respect to UVA radiation, but not so readily stabilized with respect to UVC radiation.

A photocatalyst may be added to the cabin filter itself to enhance disinfection and gas filtration. One preferred photocatalyst is titanium dioxide ($TiO_2$), although other suitable photocatalysts may also be used, for UVA and/or UVC radiation.

In one exemplary embodiment, the present disclosure provides a cabin filter cleaning system for a vehicle, including: a filter box adapted to be fluidly coupled to an air inlet and an air outlet and contain a cabin filter; an ultraviolet-C (UVC) lamp coupled to or disposed within the filter box and adapted to deliver UVC radiation to an interior portion of the filter box and the cabin filter, thereby disinfecting the cabin filter; and an ultraviolet-A (UVA) lamp coupled to or disposed within the filter box and adapted to deliver UVA radiation to the interior portion of the filter box and the cabin filter, thereby gas filtering an air flow through the cabin filter. The filter box is adapted to be disposed within one of an engine compartment and a passenger compartment of the vehicle. The air inlet includes an air intake and air intake flaps. The air outlet includes an evaporator and a blower. Optionally, the cabin filter incorporates activated carbon and titanium dioxide ($TiO_2$) that is selectively photocatalyzed by one or more of the UVC radiation and the UVA radiation. Optionally, the cabin filter includes a particulate filtering layer or region, an activated carbon layer or region disposed substantially adjacent to or coincident with the particulate filtering layer or region, and a $TiO_2$ layer or region that is selectively photocatalyzed by one or more of the UVC radiation and the UVA radiation disposed substantially adjacent to or coincident with one or more of the particulate filtering layer or region and the activated carbon layer or region and adapted to be disposed substantially adjacent to one or more of the UVC lamp and the UVA lamp. The cabin filter cleaning system also includes a control unit coupled to the UVC lamp and the UVA lamp, wherein the control unit is operable for activating the UVC lamp only for a predetermined period of time, T1, after an engine of the vehicle is started and activating the UVA lamp after the predetermined period of time, T1, has elapsed.

In another exemplary embodiment, the present disclosure provides a cabin filter for a vehicle, including: a particulate filtering layer or region; an activated carbon layer or region disposed substantially adjacent to or coincident with the particulate filtering layer or region; and a titanium dioxide ($TiO_2$) layer or region that is selectively photocatalyzed by one or more of ultraviolet-C (UVC) radiation and ultraviolet-A (UVA) radiation disposed substantially adjacent to or coincident with one or more of the particulate filtering layer or region and the activated carbon layer or region and adapted to be disposed substantially adjacent to one or more of a UVC lamp and a UVA lamp coupled to or disposed within a filter box adapted to be fluidly coupled to an air inlet and an air outlet and contain the cabin filter.

In a further exemplary embodiment, the present disclosure provides a non-transitory computer-readable medium stored in a memory and executed by a processor, causing the processor to perform the steps including: after an engine of a vehicle is started, activating an ultraviolet-C (UVC) lamp coupled to or disposed within a filter box for a predetermined period of time, T1, thereby exposing a cabin filter disposed within the filter box to UVC radiation and disinfecting the cabin filter; and, after the predetermined period of time, T1, has elapsed, deactivating the UVC lamp and activating an ultraviolet-A (UVA) lamp coupled to or disposed within the filter box, thereby exposing the cabin filter disposed within the filter box to UVA radiation and gas filtering an air flow through the cabin filter. The filter box is adapted to be disposed within one of an engine compartment and a passenger compartment of the vehicle. The air inlet includes an air intake and air intake flaps. The air outlet includes an evaporator and a blower. Optionally, the cabin filter incorporates activated carbon and titanium dioxide ($TiO_2$) that is selectively photocatalyzed by one or more of the UVC radiation and the UVA radiation. Optionally, the cabin filter includes a particulate filtering layer or region, an activated carbon layer or region disposed substantially adjacent to or coincident with the particulate filtering layer or region, and a $TiO_2$ layer or region that is selectively photocatalyzed by one or more of the UVC radiation and the UVA radiation disposed substantially adjacent to or coincident with one or more of the particulate filtering layer or region and the activated carbon layer or region and adapted to be disposed substantially adjacent to one or more of the UVC lamp and the UVA lamp. Optionally, the steps also include subsequently reactivating the UVC lamp for one or more predetermined periods of time. The processor forms part of a control unit that this coupled to the UVC lamp and the UVA lamp.

BRIEF DESCRIPTION OF THE DRAWINGS

The present disclosure is illustrated and described herein with reference to the various drawings, in which like reference numbers are used to denote like system components/method steps, as appropriate, and in which.

DESCRIPTION OF EMBODIMENTS

Again, in various exemplary embodiments, the present disclosure provides systems and methods that utilize both UVA and UVC lamps to clean and disinfect a cabin filter of a vehicle, thereby preventing the cabin filter from becoming fouled for an extended period of time. By performing both gas filtration and cabin filter disinfection functions, these systems and methods mitigate: (1) the pressure drop (or flow reduction) experienced; (2) the smell breakthrough when the gas adsorbent becomes saturated; and (3) the presence of microbial growth. This is accomplished by the sequential application of UVC and UVA radiation to the cabin filter, with the UVC radiation being applied for a period of time upon vehicle startup to neutralize bacteria and fungus present in the cabin filter and the UVA radiation subsequently being applied continuously to filter the gas flowing through the cabin filter. Limiting the application of the UVC radiation in this manner prevents damage to the cabin filter that might otherwise occur, as the polymer of the cabin filter can be readily stabilized with respect to UVA radiation, but not so readily stabilized with respect to UVC radiation.

A photocatalyst may be added to the cabin filter itself to enhance disinfection and gas filtration. One preferred photocatalyst is $TiO_2$, although other suitable photocatalysts may also be used, for UVA and/or UVC radiation.

Figure 1:
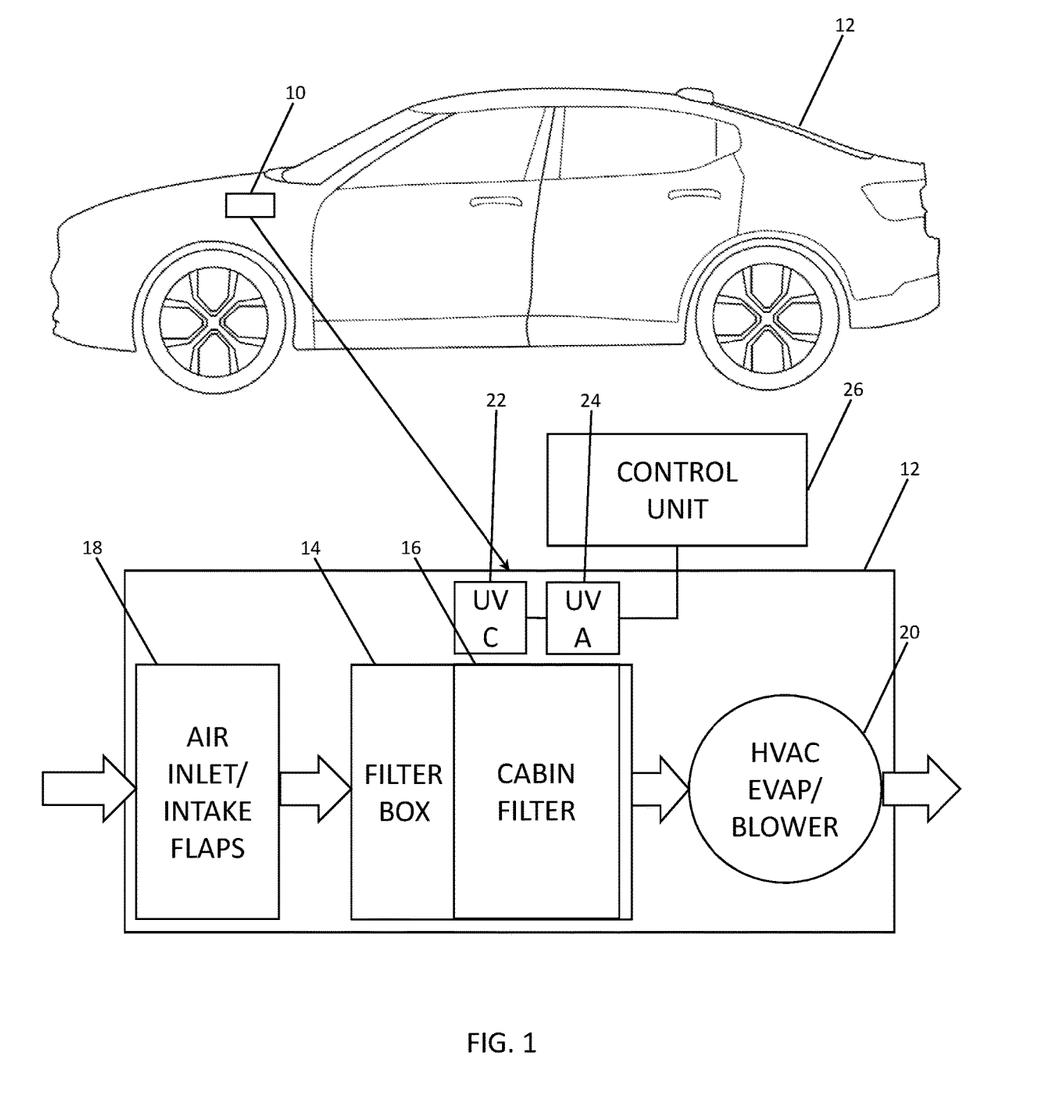
FIG. 1 is a schematic diagram illustrating one exemplary embodiment of the vehicle cabin filter cleaning system of the present disclosure, including its exemplary location within a vehicle.

Referring now specifically to FIG. 1, in one exemplary embodiment, the cabin filter cleaning system 10 of the present disclosure is generally disposed in either the engine bay or the passenger compartment of a vehicle 12. The cabin filter cleaning system 10 includes a filter box 14 that is manufactured from a substantially rigid plastic material or the like. This filter box 14 includes a removable access door or lid and contains the cabin filter 16 of the present disclosure. The cabin filter 16 consists of a removable porous filter structure in a frame, for example. Such removable porous filter structures are well known to those of ordinary skill in the art and not described in greater detail herein. Any suitable air filter may be used, although one preferred air filter is described herein. The filter box 14 forms part of the climate control system of the vehicle 12 and is generally coupled between and air inlet conduit 18 that includes conventional air intake flaps and the like and an air outlet conduit 20 that includes a conventional evaporator, blower, and the like. In operation, relatively clean air is drawn from the outside of the vehicle 12, through the filter box 14 and cabin filter 16, and into the passenger compartment of the vehicle 12. The cabin filter 16 serves to further clean the intake air as it is heated or cooled, filtering out particulates and impurities. It is thus important that the cabin filter 16 does not become plugged or fouled with bacteria and fungus, which could lead to decreased filter performance, undesirable smells, and generally lead to an unhealthy environment within the passenger compartment of the vehicle 12.

A UVC lamp 22 and a UVA lamp 24 are each coupled to or disposed within the filter box 14, such that the lamps 22,24 can deliver corresponding radiation to the interior of the filter box 14 and the cabin filter 16 without significant obstruction. The lamps 22,24 each take the form of one or more LEDs or other compact and inexpensive lamps. The lamps 22,24 are coupled to a control unit 26 that includes a processor and power source operable for selectively actuating the lamps 22,24. This control unit 26 may be disposed proximate to or remote from the filter box 14 and may incorporate components that are part of one or more other vehicle control systems.

Figure 2:
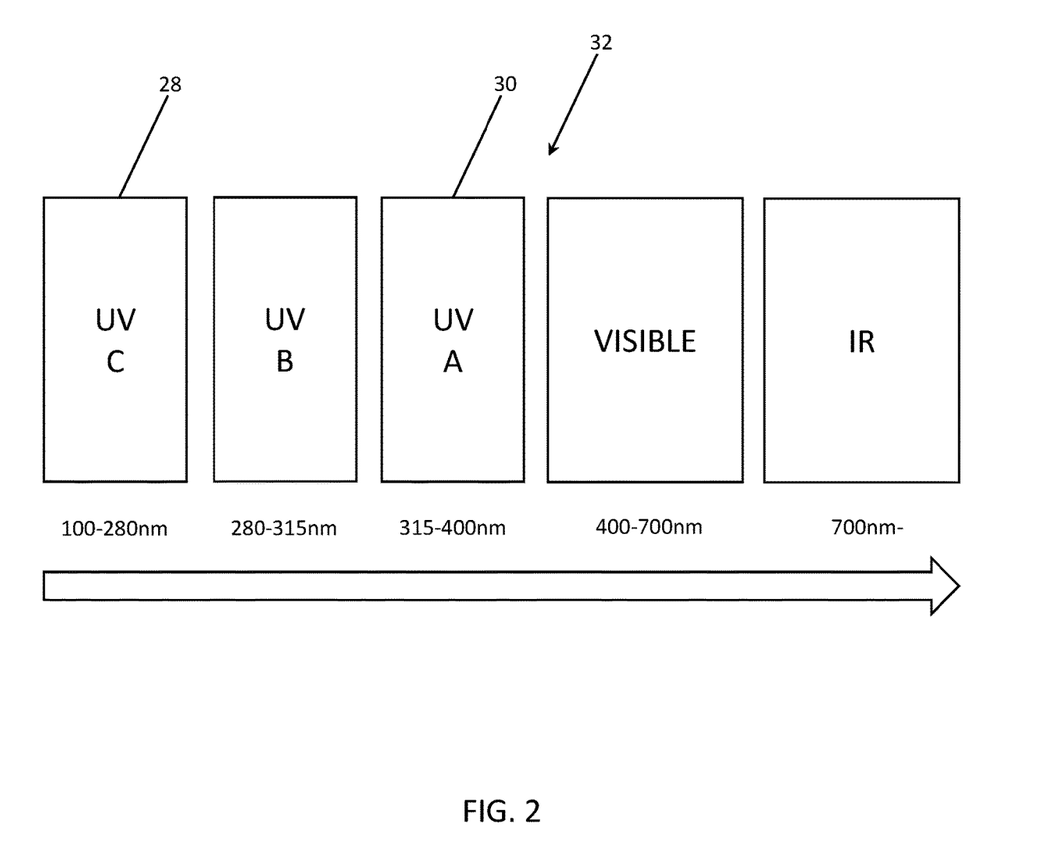
FIG. 2 is a schematic diagram illustrating the light spectrum and highlighting the UVA and UVC radiation ranges utilized by the vehicle cabin filter cleaning system and method of the present disclosure.

Referring now specifically to FIG. 2, the UVC (100-280 nm) band 28 and UVA (315-400 nm) band 30 utilized herein are shown in relation to the broader UV, visible, and infrared (IR) spectrum 32. As previously alluded to, UVC radiation emitted from a LED or other lamp can be used to disinfect the cabin filter 16 (FIG. 1) by neutralizing any harmful bacteria, viruses, or other microbial agents trapped in the cabin filter 16. Because this UVC can otherwise damage or degrade the cabin filter, exposure is limited in duration after vehicle startup. The UVA radiation is then used to gas filter the air flowing through the filter box 14 (FIG. 1) and cabin filter 16. It is well known to those of ordinary skill in the art to use UV radiation to clean carbon monoxide, hydrocarbons, and other substances and particulates from a gas flow. Advantageously, the UVA radiation is less likely to damage or degrade the cabin filter 16 than the UVC radiation. Thus, the UVA radiation can be applied continuously.

The cabin filter 16 can be impregnated with or otherwise include a photocatalyst, such as $TiO_2$ or the like, that interacts with the UVC and/or UVA radiation to enhance the disinfection and gas filtration functions provided. By way of example only, the UVC lamp 22 (FIG. 1) and the UVA lamp 24 (FIG. 1) may each be disposed about 50 mm from the cabin filter 16, which provides for effective operation and conserves space within the filter box 14. By performing both gas filtration and cabin filter disinfection functions, the systems and methods of the present disclosure mitigate: (1) the pressure drop (or flow reduction) experienced; (2) the smell breakthrough when the gas adsorbent becomes saturated; and (3) the presence of microbial growth.

Figure 3:
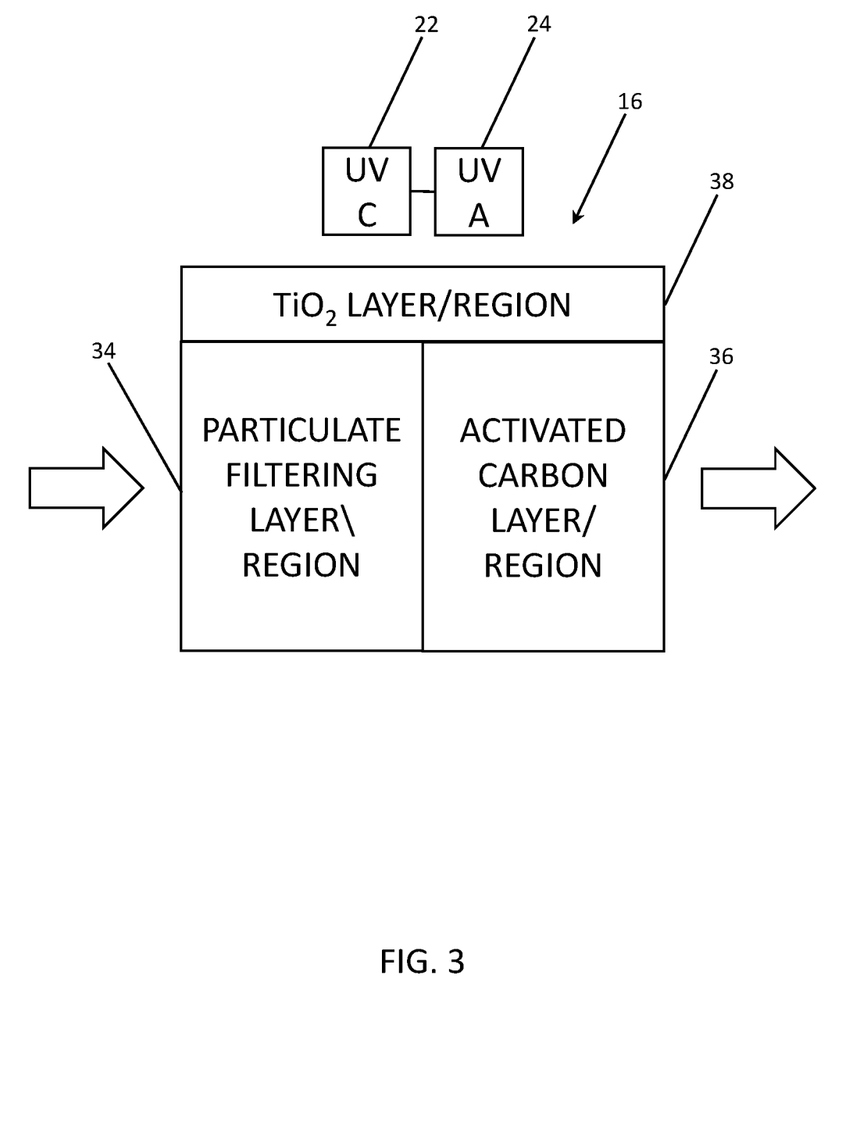
FIG. 3 is a schematic diagram illustrating one exemplary embodiment of the cabin filter of the present disclosure, utilizing particulate filtering, activated carbon, and photocatalyst layers or regions.

Referring now specifically to FIG. 3, in one exemplary embodiment, the cabin filter 16 of the present disclosure includes a particulate filtering layer or region 34, an activated carbon layer or region 36 disposed substantially adjacent to or coincident with the particulate filtering layer 34, and a $TiO_2$ layer or region 38 that is selectively photocatalyzed by one or more of the UVC radiation and the UVA radiation disposed substantially adjacent to or coincident with one or more of the particulate filtering layer or region 34 and the activated carbon layer or region 36 and adapted to be disposed substantially adjacent to one or more of the UVC lamp 22 and the UVA lamp 24. Again, by way of example only, the UVC lamp 22 and the UVA lamp 24 may each be disposed about 50 mm from the cabin filter 16, which provides for effective operation and conserves space within the filter box 14 (FIG. 1). As illustrated, the air flow through the cabin filter 16 may first encounter the particulate filtering layer or region 34, which removes particulates from the air flow, and then the activated carbon layer or region 36, which filters noxious substances from the air flow and mitigates the smell thereof, although these layers or regions 34,36 can be swapped or commingled as well. The upper (or lamp-adjacent) portion of one or both of the particulate filtering layer or region 34 and the activated carbon layer or region 36 can be impregnated with or otherwise include the $TiO_2$ or other photocatalyst, which is preferably in close proximity to the lamps 22,24.

Figure 4:
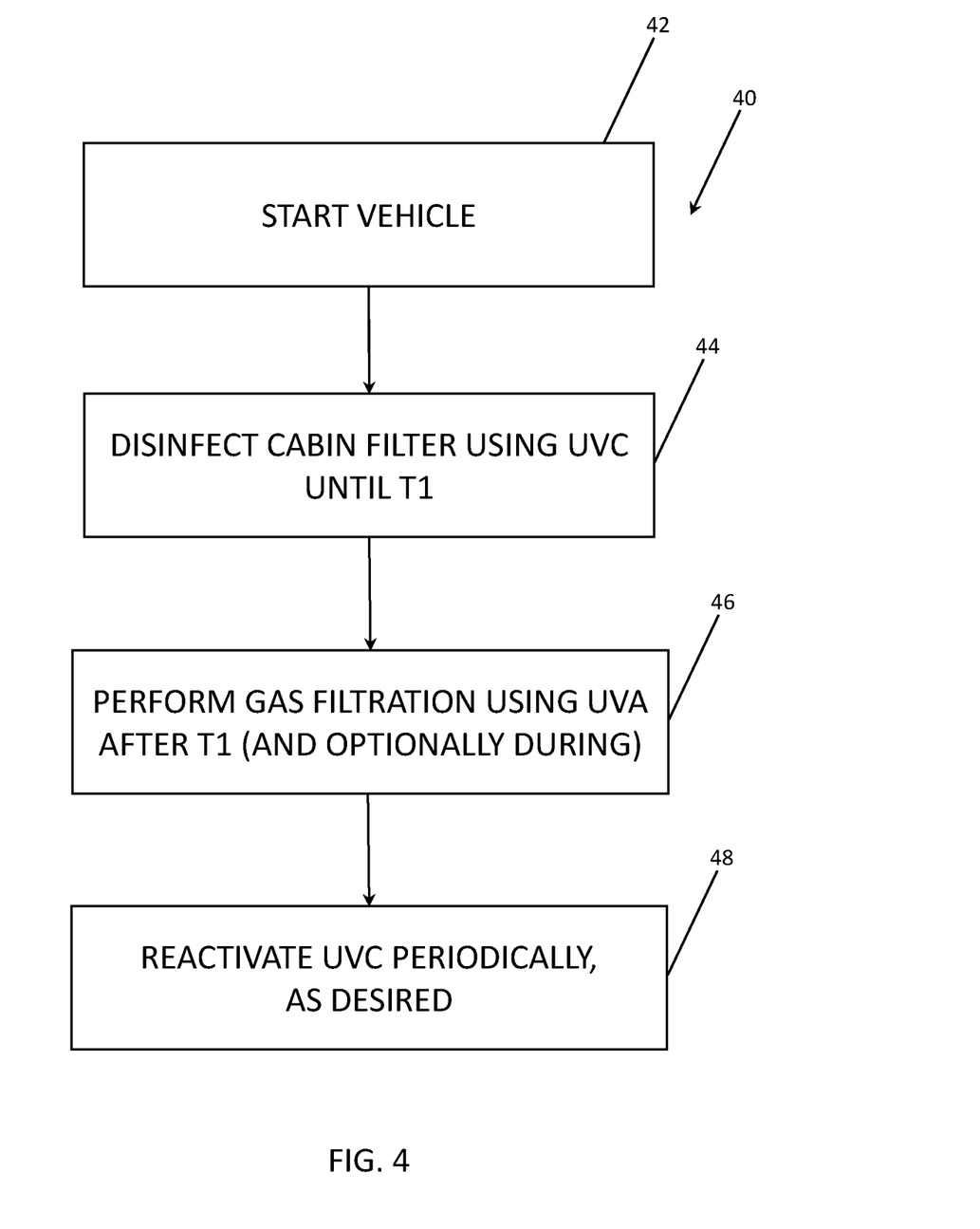
FIG. 4 is a flowchart illustrating one exemplary embodiment of the vehicle cabin filter cleaning method of the present disclosure, as implemented by software stored in a memory and executed by a processor of a vehicle control unit.

Referring now specifically to FIG. 4, in one exemplary embodiment, the cabin filter cleaning method 40 of the present disclosure is implemented by the control unit 26 (FIG. 1) and includes, after the engine of the vehicle is started (step 42), activating the UVC lamp 22 (FIGS. 1 and 3) (step 44) coupled to or disposed within the filter box 14 (FIG. 1) for a predetermined period of time, T1, thereby exposing the cabin filter 16 (FIGS. 1 and 3) disposed within the filter box 14 to the UVC radiation and disinfecting the cabin filter 16. T1 may be 2 mins, for example, or any period of time that provides disinfection but does not result in damage to or degradation of the cabin filter 16. After the predetermined period of time, T1, has elapsed, the method 40 includes deactivating the UVC lamp 22 and activating the UVA lamp 24 (FIGS. 1 and 3) (step 46) coupled to or disposed within the filter box 14, thereby exposing the cabin filter 16 disposed within the filter box 14 the to UVA radiation and gas filtering the air flow through the cabin filter 16. As the UVA radiation is not as prone to damaging or degrading the cabin filter 16 (and the cabin filter 16 can be appropriately stabilized), the UVA lamp 24 can be activated continuously from engine startup, if desired, including coincident with the UVC lamp 22. Further, the UVC lamp 22 may be reactivated periodically, as desired (step 48).

It is to be recognized that, depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) a tangible computer-readable storage medium that is non-transitory or (2) a communication medium, such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can include random-access memory (RAM), read-only memory (ROM), electrically erasable-programmable read-only memory (EEPROM), compact disc read-only memory (CD-ROM) or other optical disc storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared (IR), radio frequency (RF), and microwave, then the coaxial cable, fiber optic cable, twisted pair, DSL, or wireless technologies, such as IR, RF, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable gate arrays (FPGAs), complex programmable logic devices (CPLDs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses, including an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Thus, again, in various exemplary embodiments, the present disclosure provides systems and methods that utilize both UVA and UVC lamps to clean and disinfect a cabin filter of a vehicle, thereby preventing the cabin filter from becoming fouled for an extended period of time. By performing both gas filtration and cabin filter disinfection functions, these systems and methods mitigate: (1) the pressure drop (or flow reduction) experienced; (2) the smell breakthrough when the gas adsorbent becomes saturated; and (3) the presence of microbial growth. This is accomplished by the sequential application of UVC and UVA radiation to the cabin filter, with the UVC radiation being applied for a period of time upon vehicle startup to neutralize bacteria and fungus present in the cabin filter and the UVA radiation subsequently being applied continuously to filter the gas flowing through the cabin filter. Limiting the application of the UVC radiation in this manner prevents damage to the cabin filter that might otherwise occur.

A photocatalyst may be added to the cabin filter itself to enhance disinfection and gas filtration. One preferred photocatalyst is $TiO_2$, although other suitable photocatalysts may also be used.

Although the present disclosure is illustrated and described herein with reference to preferred embodiments and specific examples thereof, it will be readily apparent to persons of ordinary skill in the art that other embodiments and examples may perform similar functions and/or achieve like results. All such equivalent embodiments and examples are within the spirit and scope of the present invention, are contemplated thereby, and are intended to be covered by the following non-limiting claims for all purposes.

What is claimed is:

1. A cabin filter cleaning system for a vehicle, comprising:
   a filter box adapted to be fluidly coupled to an air inlet and an air outlet and contain a cabin filter;
   an ultraviolet-C (UVC) lamp coupled to or disposed within or adjacent to the filter box and adapted to deliver UVC radiation to an interior portion of the filter box and the cabin filter, thereby disinfecting the cabin filter;
   an ultraviolet-A (UVA) lamp coupled to or disposed within or adjacent to the filter box and adapted to deliver UVA radiation to the interior portion of the filter box and the cabin filter, thereby gas filtering an air flow through the cabin filter; and
   a control unit coupled to the UVC lamp and the UVA lamp, wherein the control unit is operable for activating the UVC lamp only for a predetermined period of time, T1, after an engine of the vehicle is started and activating the UVA lamp after the predetermined period of time, T1, has elapsed.

2. The cabin filter cleaning system of claim 1, wherein the filter box is adapted to be disposed within one of an engine compartment and a passenger compartment of the vehicle.

3. The cabin filter cleaning system of claim 1, where the air inlet includes an air intake and air intake flaps.

4. The cabin filter cleaning system of claim 1, where the air outlet includes an evaporator and a blower.

5. The cabin filter cleaning system of claim 1, wherein the cabin filter comprises activated carbon and titanium dioxide ($TiO_2$) that is selectively photocatalyzed by one or more of the UVC radiation and the UVA radiation.

6. The cabin filter cleaning system of claim 1, wherein the cabin filter comprises a particulate filtering layer or region, an activated carbon layer or region disposed substantially adjacent to or coincident with the particulate filtering layer, and a titanium dioxide ($TiO_2$) layer or region that is selectively photocatalyzed by one or more of the UVC radiation and the UVA radiation disposed substantially adjacent to or coincident with one or more of the particulate filtering layer or region and the activated carbon layer or region and adapted to be disposed substantially adjacent to one or more of the UVC lamp and the UVA lamp.

7. The cabin filter cleaning system of claim 1, wherein a material of the cabin filter is stabilized against damage by the UVA radiation.

8. The cabin filter cleaning system of claim 1, wherein the predetermined period of time, T1, is selected such that it is short enough that a material of the cabin filter is not damaged by the UVC radiation.

9. A cabin filter for a vehicle, comprising:
   a particulate filtering layer or region;
   an activated carbon layer or region disposed substantially adjacent to or coincident with the particulate filtering layer or region;
   a titanium dioxide ($TiO_2$) layer or region that is selectively photocatalyzed by one or more of ultraviolet-C (UVC) radiation and ultraviolet-A (UVA) radiation disposed substantially adjacent to or coincident with one or more of the particulate filtering layer or region and the activated carbon layer or region and adapted to be disposed substantially adjacent to one or more of a UVC lamp and a UVA lamp coupled to or disposed within a filter box adapted to be fluidly coupled to an air inlet and an air outlet and contain the cabin filter; and
   a control unit adapted to be coupled to the UVC lamp and the UVA lamp, wherein the control unit is operable for activating the UVC lamp only for a predetermined period of time, T1, after an engine of the vehicle is started and activating the UVA lamp after the predetermined period of time, T1, has elapsed.

10. A non-transitory computer-readable medium stored in a memory and executed by a processor, causing the processor to perform the steps comprising:
    after an engine of a vehicle is started, activating an ultraviolet-C (UVC) lamp coupled to or disposed within a filter box for a predetermined period of time, T1, thereby exposing a cabin filter disposed within the filter box to UVC radiation and disinfecting the cabin filter; and
    after the predetermined period of time, T1, has elapsed, deactivating the UVC lamp and activating an ultraviolet-A (UVA) lamp coupled to or disposed within the filter box, thereby exposing the cabin filter disposed within the filter box to UVA radiation and gas filtering an air flow through the cabin filter.

11. The non-transitory computer-readable medium of claim 10, where the filter box is adapted to be disposed within one of an engine compartment and a passenger compartment of the vehicle.

12. The non-transitory computer-readable medium of claim 10, where the air inlet includes an air intake and air intake flaps.

13. The non-transitory computer-readable medium of claim 10, where the air outlet includes an evaporator and a blower.

14. The non-transitory computer-readable medium of claim 10, where the cabin filter includes activated carbon and titanium dioxide ($TiO_2$) that is selectively photocatalyzed by one or more of the UVC radiation and the UVA radiation.

15. The non-transitory computer-readable medium of claim 10, where the cabin filter includes a particulate filtering layer or region, an activated carbon layer or region disposed substantially adjacent to or coincident with the particulate filtering layer or region, and a titanium dioxide ($TiO_2$) layer or region that is selectively photocatalyzed by one or more of the UVC radiation and the UVA radiation disposed substantially adjacent to or coincident with one or more of the particulate filtering layer or region and the activated carbon layer or region and adapted to be disposed substantially adjacent to one or more of the UVC lamp and the UVA lamp.

16. The non-transitory computer-readable medium of claim 10, further comprising subsequently reactivating the UVC lamp for one or more predetermined periods of time.

17. The non-transitory computer-readable medium of claim 10, wherein the processor forms part of a control unit that this coupled to the UVC lamp and the UVA lamp.

18. The cabin filter cleaning system of claim 1, wherein a material of the particulate filtering layer or region is stabilized against damage by the UVA radiation.

19. The non-transitory computer-readable medium of claim 10, wherein a material of the cabin filter is stabilized against damage by the UVA radiation.

20. The non-transitory computer-readable medium of claim 10, wherein the predetermined period of time, T1, is selected such that it is short enough that a material of the cabin filter is not damaged by the UVC radiation.

* * * * *